United States Patent [19]

Vinson et al.

[11] Patent Number: 4,972,719

[45] Date of Patent: Nov. 27, 1990

[54] DYNAMIC LOAD STRESS TESTER

[75] Inventors: Ted S. Vinson; Russell G. Hicks; Andrew M. Brickman; Bradford S. Whiting, all of Corvallis, Oreg.

[73] Assignee: H and V Materials Research and Development, Incorporated, Corvallis, Oreg.

[21] Appl. No.: 438,856

[22] Filed: Nov. 17, 1989

[51] Int. Cl.⁵ .............................................. G01D 7/02
[52] U.S. Cl. ...................................................... 73/790
[58] Field of Search ................... 73/789, 790, 794–796, 73/798, 818–825, 856; 33/783, 787–789

[56] References Cited

U.S. PATENT DOCUMENTS

| | | | |
|---|---|---|---|
| 2,814,883 | 12/1957 | Strimel | 33/789 |
| 3,854,328 | 12/1974 | Schmidt . | |
| 3,974,686 | 8/1976 | Van Mastrigt | 33/788 |
| 4,527,335 | 7/1985 | Meline | 33/787 |

FOREIGN PATENT DOCUMENTS

| | | | |
|---|---|---|---|
| 0372348 | 4/1973 | U.S.S.R. | 73/818 |
| 0205972 | 11/1923 | United Kingdom | 33/787 |

Primary Examiner—Robert Raevis
Attorney, Agent, or Firm—Chernoff, Vilhauer, McClung & Stenzel

[57] ABSTRACT

A test fixture to expedite the testing of the resiliency of cylindrical samples including asphalt materials. The test fixture includes a frame assembly having opposed side members for engaging the curved surface of the sample whereupon at least one transducer detects changes in displacement between the side members upon diametric deflection of the sample. Additionally, or alternatively, the test fixture includes a retaining mechanism and positioning mechanism. Upon initial alignment of the test fixture, the positioning mechanism thereafter provided automatic alignment of each consecutively tested sample with the force-applying axis. The remaining mechanism provides automatic alignment and engagement of the frame assembly with each consecutive sample.

12 Claims, 4 Drawing Sheets

DYNAMIC LOAD STRESS TESTER

BACKGROUND OF THE INVENTION

The present invention relates to a test fixture to be used in determining the resiliency of a cylindrical sample of a material, such resiliency being indicated by the diametric deflection of the sample under a dynamic load. In particular, the test fixture relates to a transducer frame engageable with the sample and to a mechanism that aligns the sample and frame for properly receiving the dynamic load along a force-applying axis. The device has particular application in measuring the resiliency of cylindrical samples of asphalt materials.

As disclosed in Schmidt, U.S. Pat. No. 3,854,328, the resiliency of a sample may be determined by applying an impulsive compressive force to the sample and measuring the resulting diametric deflection induced by the force. As Schmidt further discloses, although the transducer used to sense the deflection could be mounted on the base of a testing device, it is preferable to mount the transducer on a frame which is carried by the sample throughout the period of deflection. The transducer, then, will properly measure the diametric deflection without tangential slippage across the curved surface of the sample, as might occur were the transducer to be affixed to the base.

As shown in Schmidt, it has been customary to secure the frame to the sample by two pairs of thumb screws, one pair for engaging each of the flat end faces of the cylindrical sample. To assure proper positioning of the transducers, so that the transducers lie in a measurement plane containing the cylindrical axis of the sample, it is necessary to properly position the frame on the sample. For this purpose, a special stand has been employed into which the sample is placed and on which the frame is rested while the frame thumb screws are individually turned for engagement with the sample. However, when many samples require test, much valuable staff time is consumed by this frame orientation and engagement procedure, particularly since each thumb screw must be individually turned. Furthermore, after the frame is properly secured to the sample, each sample must then be individually oriented with the respective top and bottom loading faces so that the cylindrical axis of the sample lies substantially normal to, and aligned with, the force-applying axis, as well as parallel to the contacting edges of the loading face. Without attention to these relationships, the force-applying axis may be misaligned in relation to the frame, or the respective loading faces may be presented with variable sample surface areas during deflection, thereby distorting applied stress readings. Yet the attention that must be paid to individual orientation procedures greatly extends the test time required for each sample. To further aggravate this problem, the resiliency of any one sample is commonly measured along two axis of the sample, each perpendicular to the other, thus doubling the required set-up times.

What is required, then, is a test fixture that will measure the diametric deflection of many samples successively without a large time expenditure for individual frame and sample orientation and engagement.

SUMMARY OF THE INVENTION

A first aspect of the present invention provides side members that engage the curved surface of the sample and that are yieldably biased for rapid placement of the frame on the sample while still permitting deflection to occur and be measured. Reliance on individual screws, to attach the frame to the sample, is thereby avoided. In a particular embodiment, the transducers indirectly measure the movement of the curved surface by measuring the change in displacement between the side members rather than directly contacting the curved surface itself. An additional preferred feature includes a retaining mechanism whereby the biased side members are selectively held away from, or released against, the curved surface of the sample. This allows the side members to be biased against the sample with greater force, and hence more security, than would be possible if the frame were required to yield to unaided manual pulling of the yieldable side members.

A second aspect is a positioning mechanism serving to orient the sample relative to the force-applying axis induced between the loading face and the force-applying member while allowing movement of the sample between an initial seating position and a final seating position. Preferably the positioning mechanism is movably synchronized with the retaining mechanism to permit free rotation of the sample, for measurement of sample resiliency along different sections of the sample, while the frame is held away from the sample, and to ensure the frame will be properly oriented with respect to the sample when the frame is released against the sample.

A third aspect of the present invention is the ability of the positioning mechanism to properly orient both the sample and the frame relative to the force-applying axis irrespective of whether the frame is yieldably biased or whether a retaining mechanism is employed for convenient engagement of the frame.

DETAILED DESCRIPTION OF THE INVENTION

Figure 1:
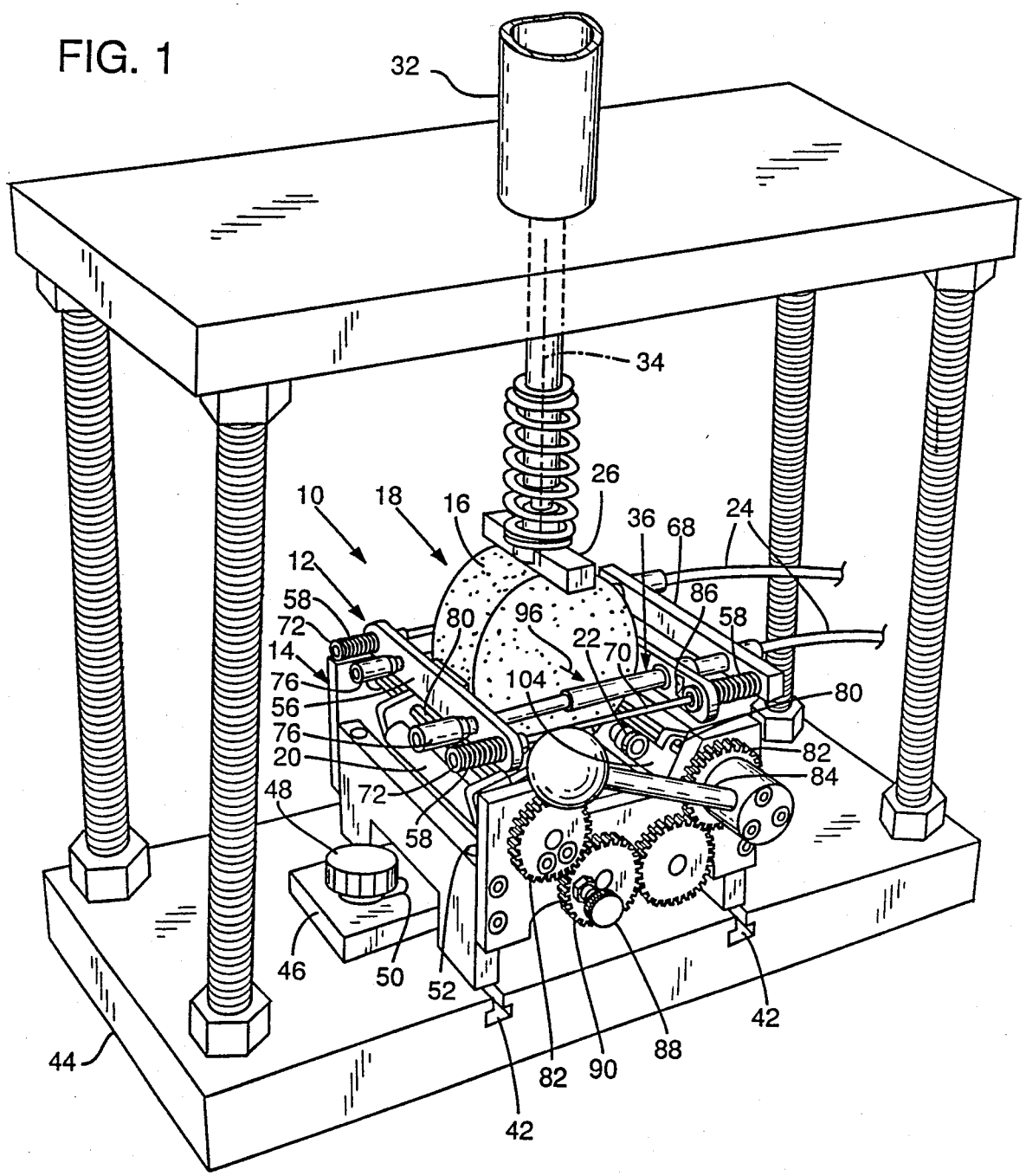
FIG. 1 is a perspective view of an exemplary embodiment of a dynamic load stress tester, in accord with the present invention, set to measure the horizontal diametric deflection of a cylindrical sample upon application of a vertical dynamic load.

FIG. 1 illustrates a specific embodiment of a dynamic load stress tester 10 constructed in accordance with the present invention. The dynamic load stress tester 10 comprises a frame assembly 12 and a base assembly 14 that may each be operated alone or in combination with each other.

FIG. 1 illustrates the dynamic load stress tester 10 set for measurement of the diametric deflection of the sample 18. The frame assembly 12 engages the curved surface 16 of the cylindrical sample 18, while the positioning rollers 20 and retaining knobs 22 (one of each being visible in FIG. 1) are shown in their inoperative, retracted testing positions. As further indicated by the dashed lines of FIG. 4, in their inoperative testing position the positioning rollers 20 and retaining knobs 22 are fully disengaged from the sample or frame. Due to a static load induced by pneumatic driver 32, the sample is fixedly held between the top load strip, or force-applying member 26, and the loading face 28 of the bottom loading strip 30.

To measure the resiliency of a particular sample 18 the user sends an appropriate control signal to the pneumatic driver 32. The pneumatic driver then causes a downward urging of the force-applying member 26 toward the loading face 28 of the bottom loading strip 30 thereby establishing a dynamic stress in the sample along the force-applying axis 34. This dynamic stress, while increasing, causes an outwardly directed diametric deflection of the sample 18, the extent of such deflection being a function of the sample resiliency. Transducers 36 on the frame assembly 12 measure the resulting deflection or strain, while transducers contained in the bottom load cell 38 (FIG. 4) measure the applied dynamic load.

During the above-described measurements, correct alignment of the sample 18 relative to the force-applying member 26 and loading face 28 is important. Also important is correct alignment of the frame assembly 12 relative to the sample 18. It has been conventional in the past to make such alignments manually for each sample tested. Described, hereafter, is an exemplary frame assembly 12 and base assembly 14, permitting such alignments to be made automatically after one time alignment of the base assembly during initial setup. More specifically, the base assembly 14 provides a retaining mechanism for automatic frame alignment and engagement and a positioning mechanism for automatic sample alignment.

Referring again to FIGS. 1 and 4, initial alignment begins by sliding the threaded legs 40 of the base assembly 14 into the leg slots 42 provided on the test frame 44. This ensures that the base assembly 14 is centered relative to the force-applying member 26. Next, the load cell support 46, carrying bottom load strip 30 and bottom load cell 38, is slid beneath the base assembly 14. Hand knobs 48 are passed through guide slots 50 in the load cell support 46 into threaded holes (not shown) in the test frame 44 (only the left knob and left guide slot are visible in FIG. 1). After the bottom load strip 30 has been positioned to directly oppose the top load strip or force-applying member 26, hand knobs 48 are tightened to secure this position. By passing a screwdriver through leg adjustment holes 52 each screw head 54 of a threaded leg 40 may be turned, as needed, to level the base assembly with the flat loading face 28 of the bottom load strip 30. This completes alignment of the base assembly 14 with the loading face 28 and the force-applying member 26.

Figure 3:
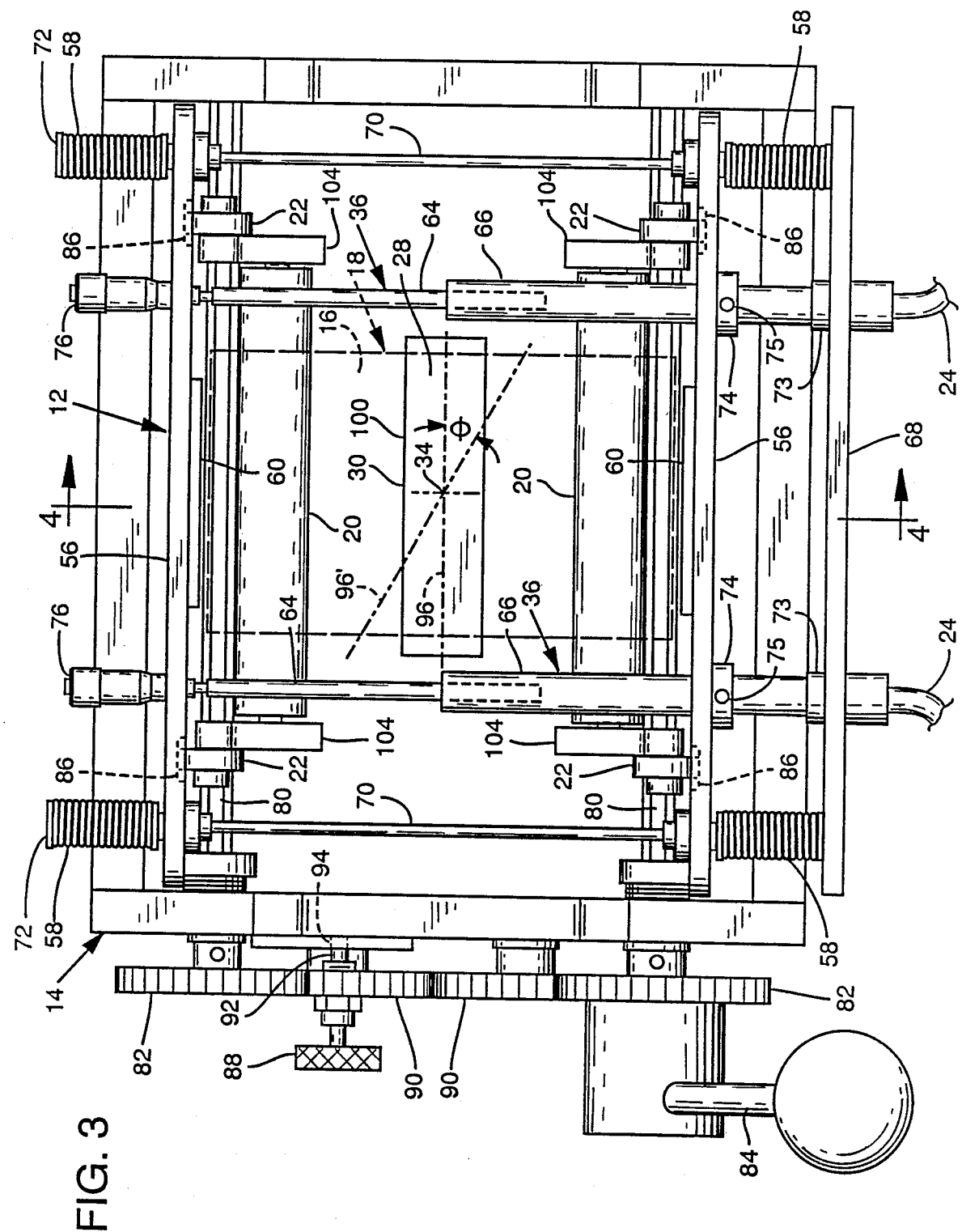
FIG. 3 is a plan view of the exemplary dynamic load stress tester set for initial sample support.

In FIG. 3, an exemplary embodiment of the frame assembly 12 is presented from a plan view. Retaining knobs 22, being a part of the base assembly 14, are shown as holding the frame 12 in a fully opened position. The frame 12 includes a pair of opposed side members 56 that are movable alternatively toward and away from each other so as to engage and disengage the curved surface 16 of a cylindrical sample 18, such surface here being represented by dashed lines. This approach is in contrast to conventional methods where transducers on the frame, not the frame itself, engage the curved surface of the sample.

For the exemplary frame assembly shown, the side members 56 are yieldably biased toward each other by springs 58. These springs must be light enough to allow outward displacement of the side members 56 upon outward deflection of the curved surface 16 of the sample, yet they must be heavy enough so that the side members 56 do not slip tangentially across the curved surface 16 upon reversal of the deflection path. To further prevent tangential slippage, a curved nonskid face 60, made of material having the roughness of sandpaper, is provided on the side members 56.

To detect changes in displacement between the opposed side members 56, upon diametric deflection of the sample, a pair of transducers 36 are employed. The transducers constitute conventional linear variable differential transformers (LVDTs) that measure the depth of insertion of the LVDT piston 64 into the LVDT sleeve 66. Diametric deflection of the curved surface 16 of the sample is thus measured indirectly, by measuring the displacement of the side members 56, as contrasted with the conventional approach where the transducers directly engage the curved surface 16 of the sample.

The exemplary frame assembly 12 shown in FIG. 3 may be constructed in the following manner. A back support 68 having two legs 70 extending normally therefrom provides support for the remaining elements of the frame assembly 12. A spring 58 is slipped onto each leg 70 followed by a pair of side members 56 and another spring 58. End pieces 72 affixed to the legs 70 prevent the springs 58 and side members 56 from sliding off the legs 70. Next transducers 62 are slideably inserted through the pair of collars 73 provided in the back support 68 and are affixed one of the side members 56 by tightening of the screws 75 that completely pass through holes (not shown) in side member collars 74. Thumbscrew micrometers 76 are then fixedly inserted into the pair of holes provided in the other side member 56. After the side members 56 have been released against the curved surface 16 of the sample these micrometers 76 adjust the insertion depth of the transducer pistons 64 into the transducer sleeves 66 so as to establish a zero or null signal to the transducer sensor wires 24 for the particular sample being tested.

A substantial advantage of the exemplary frame assembly 12 over prior frame assemblies is the speed with which the frame assembly may be positioned on the sample due to the use of springs 58. As noted above, however, the springs must be made relatively heavy to maintain engagement of the side members 56 with the curved surface 16 of the sample upon reversal of the deflection path. For the user to manually pull apart the side members 60, given the heavy springs 58 that are required, involves much physical strength, and the user's fingers, being wrapped around the side members 56, interfere in the alignment of the frame 12 with the sample 18. For these reasons, it is preferable to use a selectively actuated retaining mechanism that alternatively holds the side members 56 outwardly from, or releases the side members 56 into engagement against, the curved surface 16 of the sample 18.

Figure 2:
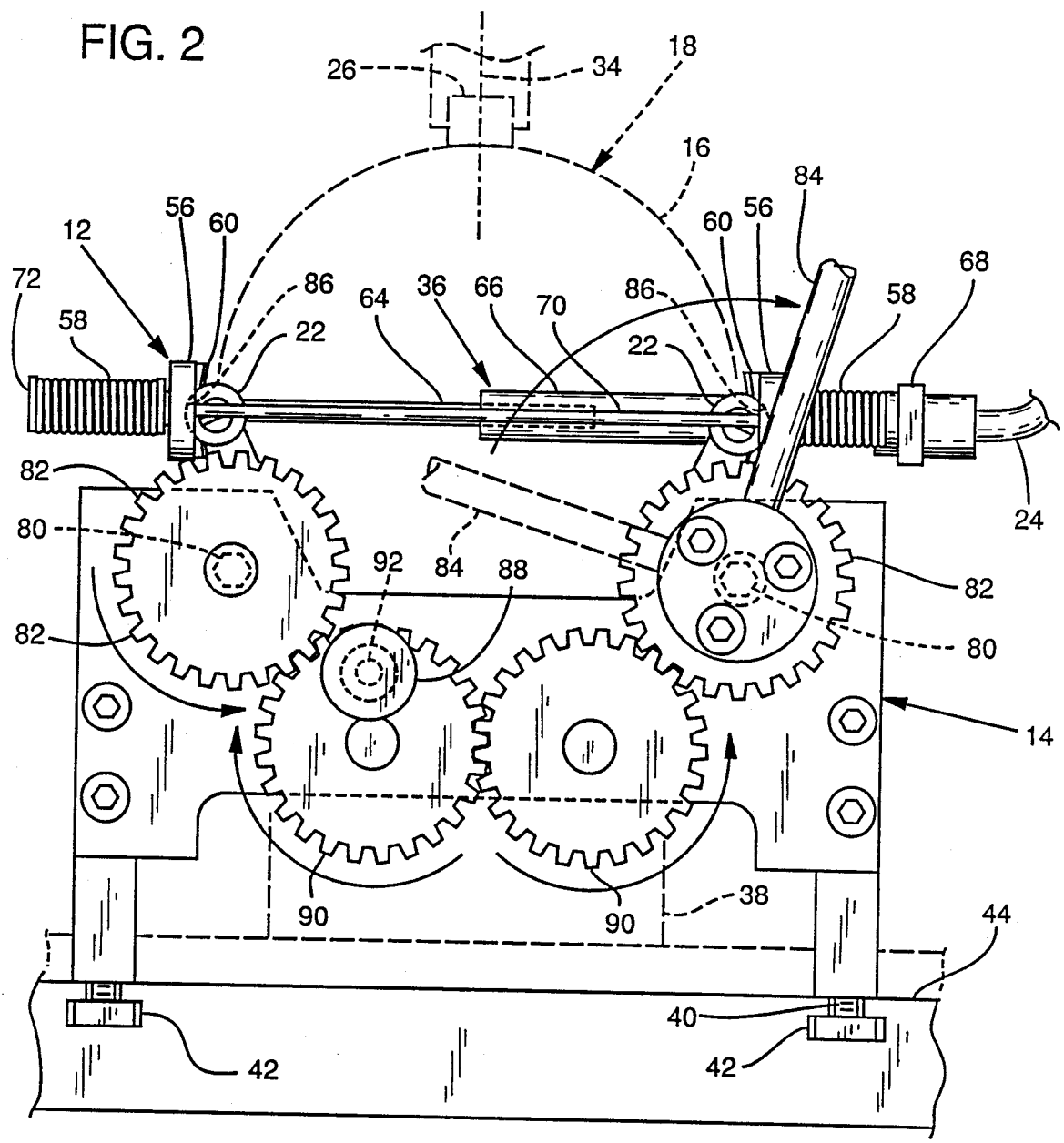
FIG. 2 is a front view of the exemplary dynamic load stress tester, with some portions removed to show the underlying structure.

For the exemplary invention depicted in FIGS. 1-4, the selectively actuated retaining mechanism includes four retaining knobs 22 with each pair of retaining knobs connected to a left or right turning rod 80 connected, in turn, to a left or right turning gear 82. Referring to FIG. 2, it may be seen that a clockwise pull on handle arm 84 causes the left and right turning rods 80 to rotate in opposite directions. This, in turn, causes the left and right pairs of retaining knobs 22 to move upward and outward from each other and to engage a respective opposed side member 56, thereby holding the side members outwardly from the curved surface 16 of the sample 18. Pulling the handle arm 84 in the counterclockwise direction will cause the left and right turning rods 80 to turn oppositely so as to bring the left and right pairs of retaining knobs 22 toward one another so that the left and right side members are released into engagement against the curved surface 16 of the sample as shown by the solid lines in FIG. 4. Further counterclockwise motion of the handle arm 84 eventually brings the left and right pair of retaining knobs 22 into the inoperative, retracted testing position indicated by the dashed lines in FIG. 4. In this retracted position, the retaining knobs 22 do not interfere with measurement of the deflection of the side members 56.

The retaining mechanism just described represents one suitable embodiment. Other approaches may be used to hold the side members 56 outwardly from, and release the side members 56 into engagement against, the curved surface 16 of the sample. For example, a pneumatic piston may be connected between the side members 56 that, upon user command, holds or releases the side members. Such a piston may remain engaged with the side members 56 at all times without disturbing the outward deflection of the side members 56.

Referring to FIGS. 1 and 3, to ensure that the left and right pairs of retaining knobs 22 properly engage the side members 56 as the handle arm 84 is turned clockwise, a left and right pair of concave depressions 86 are provided on the left and right side members 56. Additionally, the left and right pair of retaining knobs 22 are rotatable and therefore will tend to roll into the deepest portion of the depressions 86 thereby aligning the frame 12 with the retaining knobs 22.

Referring to FIGS. 1 and 3, a further feature of the retaining mechanism is lock knob 88. With the lever arm 84 fully clockwise, the retaining knobs 22 press outwardly against the side members 56, and the curved surface 16 of the sample 18 may then be positioned therebetween. It is convenient to lock the side members 56 in this outward position from the curved surface 16 of the sample so that both hands may be used to position the sample. Lock knob 88 performs this function. Specifically, referring also to FIG. 2, as the handle arm 84 is turned fully clockwise, the lock knob 88, mounted on center gear 90, moves in a clockwise direction in a circular path. At the fully clockwise position of the handle arm 84, the terminal end 92 of the lock knob 88 encounters a knob hole 94 (FIG. 3) drilled into the base assembly 14. Internal springs in the lock knob 88 force its terminal end 92 into the knob hole 94 thereby preventing further movement of the center gears 90, the turning gears 82, the turning rods 80, and ultimately the retaining arms 22. After the curved surface 16 of the sample has been properly positioned the user may hold handle arm 84, pull lock knob 88 away from the knob hole 94, and gradually loosen his hold on lever arm 84 to permit the side members 56 to engage the curved surface 16 of the sample.

In addition to a retaining mechanism, the base assembly 14 also includes a positioning mechanism. FIG. 3 depicts the base assembly 14 when the handle arm 84 is in fully clockwise position and the left and right positioning rollers 20 are ready to receive the curved surface 16 of a sample. It will be recognized that centering of the loading face 28 relative to the base assembly 14, during initial setup as described above, also results in centering of the loading face 28 relative to the positioning rollers 20. Therefore, the cylindrical axis 96 of a sample 18 placed on the positioning rollers 20 will be aligned with the center of the loading face 28 or with the force-applying axis 34.

Figure 4:
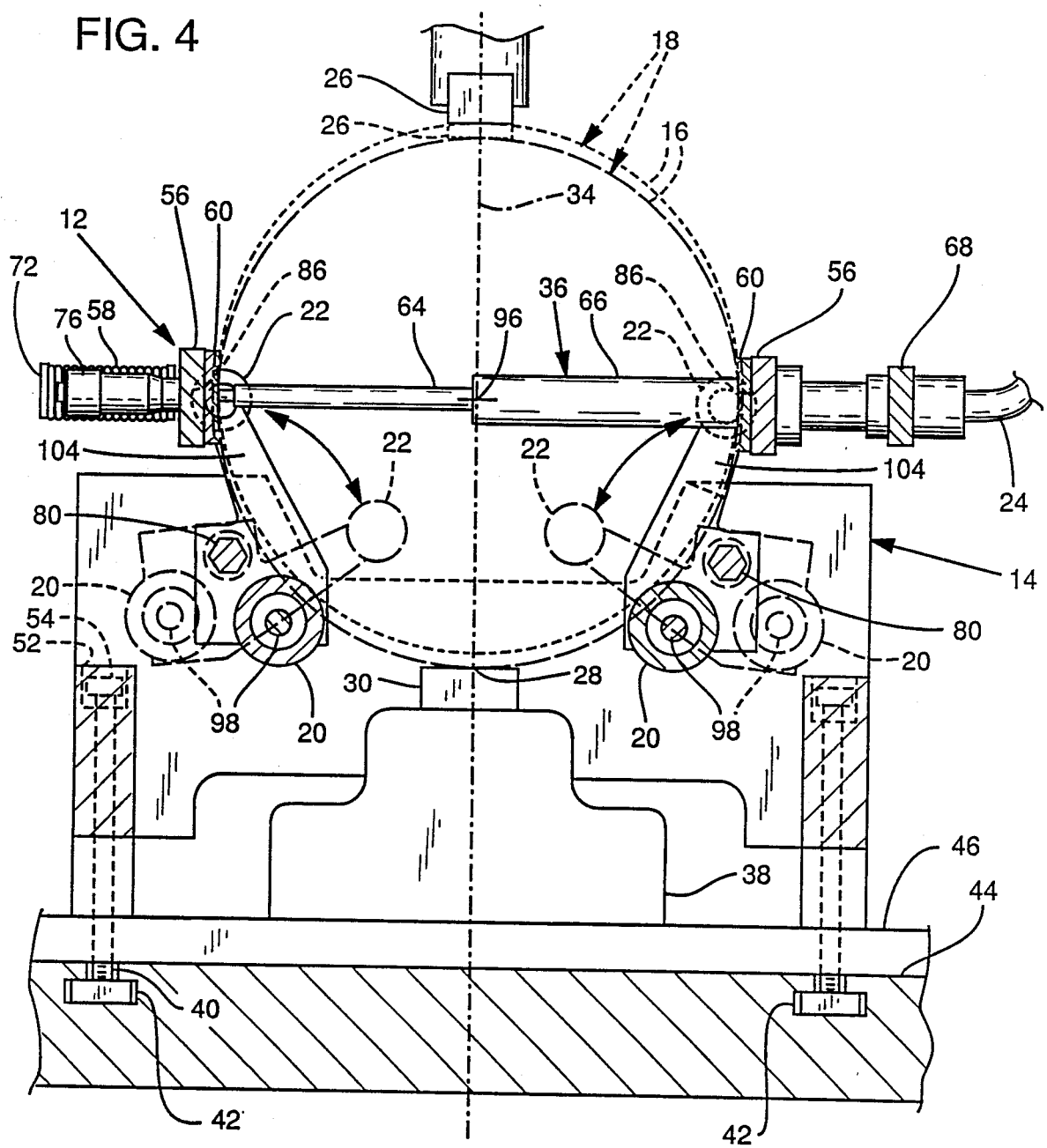
FIG. 4 is a sectional view of the exemplary dynamic load stress tester, taken along line 4—4 of FIG. 3, the lightly dashed outline of the sample indicating the intermediate seating position thereof and the heavy dashed outline of the sample indicating the testing position thereof. The inoperative, retracted position of the retaining and positioning mechanisms are shown in dashed lines.

The positioning rollers 20 hold the sample 18 above the loading face 28. Referring also to FIG. 4, if the threaded legs 40 have been properly adjusted during initial setup, when the sample 18 rests on the positioning rollers 20 the cylindrical axis 96 should be substantially normal to the force-applying axis 34.

Referring again to FIGS. 3 and 4, the left and right positioning rollers 20 are freely rotatable about the left and right roller shafts 98, respectively. Therefore, if a sample 18 is placed on the positioning rollers 20 at a skewed angle, such that the cylindrical axis 96' of the sample is skewed relative to its predetermined rotational orientation, the positioning rollers 20 will tend to spin so that the final cylindrical axis 96 of the sample is aligned with the predetermined rotational orientation. This orientation will generally be parallel to the contacting edges 100 of the loading face 28.

From the above discussion, it may be recognized that after initial setup of the base assembly 14, each individual sample is thereafter automatically aligned relative to the loading face 28. If the cylindrical axis 96 of the sample 18 were skewed relative to the loading face 28, the stress measurement could be inaccurate because variable areas of the sample's curved surface 16 would come in contact with the loading face 28 upon application of a dynamic load.

In the initial seating position depicted in FIG. 3, the curved surface 16 of the sample 18 is supported out of contact with the loading face 28. In this position, the free rotation of the positioning rollers 20 about roller shafts 98 allows rotation of the sample 18 about its own cylindrical axis 96. After a sample has been tested along one section, the sample may be rotated 90° about its cylindrical axis so that another section of the sample may be measured for resiliency. During this procedure, the retaining knobs 22 hold the side members 56 away from the curved surface 16 of the sample. It will be recognized that this selection process is performed without disturbing the alignment of the sample.

After initial setup of the base assembly 14 and the loading face 28, and after the sample 18 has been placed on the positioning rollers 20 while the handle arm 84 in fully clockwise position, engagement of the sample 18 by the frame assembly 12 may occur. The force-applying member 26 is placed on top of the sample in directly opposing relationship to the loading face 28. A nominal static load, being approximately 5% of the expected dynamic load, is then exerted on the sample 18 through the force-applying member 26. Referring to FIG. 3, handle arm 84 is gripped while lock knob 88 is pulled away from knob hole 94. This induces a counterclockwise pressure on handle arm 84 due to the pressure of the frame springs 58 acting on the retaining knobs 22 and the pressure of the statically loaded sample 18 on the positioning rollers 20. Handle arm 84 is gradually released to permit movement in this counterclockwise direction, until retaining knobs 22 release the side members 56 into engagement with the curved surface 16 of the sample 18. This engagement is illustrated in FIG. 4 by the solid line elements of the frame assembly 12 and base assembly 14 and by the lightly dashed outline of the sample 18. At this position, the curved surface 16 of the sample 18 is supported by positioning rollers 20 at an intermediate seating position.

The side members 56 engage the curved surface 16 of the sample along a predetermined orientation with respect to the force-applying axis 34. Specifically, the measurement plane extending horizontally from the middle of the left side member 56 to the middle of the right side member 56 lies substantially normal to the force-applying axis 34. This normal relationship occurs because each retaining knob 22 is similarly attached to a respective turning rod 80, and the pair of turning rods 80 were aligned with the force-applying axis 34 when the base assembly 14 was leveled during initial setup. Having a measurement plane normal to the force-applying axis 34 allows accurate measurement of a sample's horizontal strain upon application of a dynamic vertical load.

The left and right pairs of retaining knobs 22 are connected to the left and right positioning rollers 20, respectively, by the left and right lever arms 104. Therefore the retaining knobs 22 are movably synchronized with the positioning rollers 20. Their relative positions are such that a full diameter of the sample 18 will be presented to the side members 56 as the side members 56 are released into engagement against the sample 18. Stated differently, the measurement plane extends through the cylindrical axis 96 of the sample 18. Without proper alignment of the frame relative to the force-applying axis 34 or the sample cylindrical axis 96, the strain measurement may be inaccurate due to uneven deflection of the curved surface 16 between the pair of regions selected.

At the point of engagement of the side members 56 with the curved surface 16, not only the frame assembly 12 but also the sample 18 itself will be in proper predetermined orientation with respect to the force-applying axis 34. Referring again to the specific embodiment depicted in FIG. 4, the positioning rollers 20 maintain their level relationship with the loading face 28 even as they are moved from their initial supporting position to their intermediate seating position shown in solid lines. Therefore the cylindrical axis 96 of the sample remains in substantially normal relationship to the force-applying axis 34. Referring again to FIG. 2, because the turning gears 82 and center gears 90 are equally dimensioned, the left and right turning rods 80 will rotate at equal rates upon movement of the handle arm 84. This ensures that the positioning rollers 20 move equal distances away from the center of the base assembly 14 so that the cylindrical axis 96 of the sample 18 is maintained in alignment with the force-applying axis 34. Because the positioning rollers 20 always maintain their parallel relationship, the rotational orientation of the cylindrical axis 96 of the sample 18 about the force-applying axis 34 is preserved.

After the side members 56 have been released into engagement against the curved surface 16 of the sample 18, gradual release of handle arm 84 is continued to permit further movement in a counterclockwise direction. Referring again to FIG. 4, the positioning rollers 20 here represented in dashed lines, will bring the sample 18, here represented by heavy dashed lines, to a final seating position for testing, wherein the curved surface 16 of the sample 18 comes to rest against, or in contact with, the loading face 28. For reasons similar to those just provided, the cylindrical axis 96 of the sample 18 will maintain its alignment with the force-applying axis 34.

During movement of the sample 18, from the intermediate seating position to the final seating position, the retaining knobs 22 will become detached from the side members 56. An unbalanced weight distribution on the frame, caused by the transducers 36 and transducer wires 24, tends to tilt the frame 12 to one side. However, the static load force exerted by the force-applying member 26 in conjunction with the counteracting forces exerted on the sample by the positioning rollers 20 prevent this tilt of the frame 12. Therefore, the measurement plane extending between the side members 56 remains substantially normal to the force-applying axis 34 as the curved surface 16 of the sample 18 comes to rest against the loading face 28.

Once the retaining knobs 22 are detached from the side members 56, and once the positioning rollers 20 have brought the sample 18 to its final seating position, there is no longer any counterclockwise pressure on the handle arm 84. Further counterclockwise movement of the handle arm 84 places the retaining knobs 22 and positioning rollers 20 in their inoperative, retracted testing positions as indicated by the dashed lines in FIG. 4. These retracted positions may also be seen in FIG. 1. A dynamic force may now be exerted on the sample, through the force-applying member 26, and the resulting diametric deflection of the sample measured.

After measurement is completed on a particular section of a particular sample, the static load may be removed and the force-applying member 26 lifted off the sample. Returning the handle arm 84 to its fully clockwise position reopens the frame and resets the positioning rollers 20 for initial support of the sample 18 so that a different rotational section of the sample can be selected for test. Alternatively, a new sample 18 may be set in the base assembly 14 for automatic alignment, frame engagement, and test. In this manner, expedited testing of many consecutive samples is possible.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A test fixture for measuring diametric deflection of the curved surface of a cylindrical sample under a predetermined load, said test fixture comprising:
   (a) a frame including a support member and a pair of spaced-apart elongate leg members extending normally therefrom, and a pair of opposed side members each being slidably mounted on said pair of leg members and extending therebetween for guided translational movement therealong;
   (b) biasing means interacting with said side members for resiliently biasing said side members toward each other so that said curved surface is engaged by said side members and held therebetween; and
   (c) at least one transducer mounted between both of said side members for detecting change in displacement therebetween upon diametric deflection of said sample.

2. A test fixture as recited in claim 1 further comprising a selectively actuated retaining means engageable with the side members of said frame for alternatively holding said side members outwardly from, and releasing said side members into engagement against, the curved surface of said sample.

3. A test fixture for measuring diametric deflection of the curved surface of a cylindrical sample under a predetermined load induced on said sample along a force-applying axis between a force-applying member and a loading face, said test fixture comprising:
(a) positioning means for holding the curved surface of said sample in an initial seating position out of contact with said loading face while holding the cylindrical axis of said sample in substantially normal intersecting relationship with said force-applying axis;
(b) said positioning means further including means for moving said sample from said initial seating position to a final seating position where the curved surface of said sample is in contact with said loading face, while concurrently maintaining said substantially normal intersecting relationship.

4. A test fixture as recited in claim 3 wherein said positioning means includes a base and a pair of elongate support members mounted on said base in parallel spaced-apart alignment with each other, said support members together forming said holding means, and wherein said moving means includes means linking together said support members for causing synchronous movement of said support members away from each other so as to cause movement of said sample from said initial seating position to said final seating position.

5. A test fixture as recited in claim 4 further comprising rotatable means on each of said support members for supporting said sample in said initial seating position while positioning said cylindrical axis in parallel orientation with said support members and allowing free rotation of said sample about said cylindrical axis.

6. A test fixture for measuring diametric deflection of the curved surface of a cylindrical sample under a predetermined load, said test fixture comprising:
(a) a frame including a pair of opposed side members;
(b) biasing means interacting with said side members for yieldably biasing said side members toward each other so that said curved surface is engaged by said side members and held therebetween;
(c) at least one transducer communicating with both of said side members for detecting change in displacement therebetween upon diametric deflection of said sample; and
(d) a selectively actuated retaining means selectively detachably engageable with said members for alternatively holding said side members outwardly from, and releasing said side members into engagement against, the curved surface of said sample.

7. A test fixture for measuring diametric deflection of the curved surface of a cylindrical sample under a predetermined load, said test fixture comprising:
(a) a frame including a pair of opposed side members;
(b) biasing means interacting with said side members for yieldably biasing said side members toward each other so that said curved surface is engaged by said side members and held therebetween;
(c) at least one transducer communicating with both of said side members for detecting change in displacement therebetween upon diametric deflection of said sample;
(d) a selectively actuated retaining means engageable with the side members of said frame for alternatively holding said side members outwardly from, and releasing said side members into engagement against, the curved surface of said sample; and
(e) positioning means movably synchronized with said retaining means for positioning said cylindrical sample and said side members with respect to each other while said side members are held outwardly from said curved surface so that said side members are separated by a full diameter of said sample after said side members are released into engagement against said curved surface.

8. A test fixture as recited in claim 7 further comprising sample supporting means on said positioning means for supporting said ample while allowing free rotation of said sample about its cylindrical axis when said side members are held outwardly from said curved surface.

9. A test fixture for measuring diametric deflection of the curved surface of a cylindrical sample under a predetermined load, said test fixture comprising:
(a) a frame including a pair of opposed side members;
(b) biasing means interacting with said side members for yieldably biasing said side members toward each other so that said curved surface is engaged by said side members and held therebetween;
(c) at least one transducer communicating with both of said side members for detecting change in displacement therebetween upon diametric deflection of said sample;
(d) a selectively actuated retaining means engageable with the side members of said frame for alternatively holding said side members outwardly from, and releasing said side members into engagement against, the curved surface of said sample; and
(e) means for inducing said predetermined load on said sample along a force-applying axis between a force-applying member and a loading face, and positioning means for positioning said cylindrical sample and said side members with respect to each other while said side members are held outwardly from said curved surface so that said side members are in a predetermined orientation with respect to said force-applying axis as said side members are released into engagement against said curved surface.

10. A test fixture as recited in claim 9 wherein said predetermined orientation is such that said side members are separated substantially by a diameter of said cylindrical sample which extends perpendicularly to said force-applying axis.

11. A test fixture as recited in claim 10 further comprising measurement plane maintaining means located on said positioning means for maintaining said measurement plane substantially normal to said force-applying axis after said side members have been released into engagement against said curved surface and as said curved surface comes to rest against said loading face.

12. A test fixture as recited in claim 9 wherein said predetermined orientation is such that said changes in displacement between said side members occurs along a measurement plane extending substantially normal to said force-applying axis.

* * * * *

UNITED STATES PATENT AND TRADEMARK OFFICE
CERTIFICATE OF CORRECTION

PATENT NO.  : 4,972,719

DATED       : November 27, 1990

INVENTOR(S) : Ted S. Vinson, et al.

It is certified that error appears in the above-identified patent and that said Letters Patent is hereby corrected as shown below:

On the title page in the Abstract:

Line 10, change "provided" to --provides--;

Column 4, line 35, after "affixed" insert --to--.

Column 10, line 18, change "ample" to --sample--.

Signed and Sealed this

Fifteenth Day of September, 1992

Attest:

DOUGLAS B. COMER

*Attesting Officer*    *Acting Commissioner of Patents and Trademarks*